US007173000B2

(12) United States Patent
Ruf et al.

(10) Patent No.: US 7,173,000 B2
(45) Date of Patent: Feb. 6, 2007

(54) MODIFIED FACTOR VIIA

(75) Inventors: Wolfram Ruf, San Diego, CA (US); Ramona J. Petrovan, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 433 days.

(21) Appl. No.: 10/415,963

(22) PCT Filed: Nov. 9, 2001

(86) PCT No.: PCT/US01/47329

§ 371 (c)(1),
(2), (4) Date: May 5, 2003

(87) PCT Pub. No.: WO02/38162

PCT Pub. Date: May 16, 2002

(65) Prior Publication Data
US 2004/0033566 A1 Feb. 19, 2004

Related U.S. Application Data

(60) Provisional application No. 60/247,589, filed on Nov. 9, 2000.

(51) Int. Cl.
```
A61K 35/14     (2006.01)
A61K 38/00     (2006.01)
C07H 21/04     (2006.01)
C12N 15/63     (2006.01)
C12N 1/20      (2006.01)
C07K 1/00      (2006.01)
```
(52) U.S. Cl. .................. 514/2; 530/384; 536/23.1; 435/320.1; 435/252.3; 435/69.6

(58) Field of Classification Search .................. None
See application file for complete search history.

(56) References Cited

U.S. PATENT DOCUMENTS

| | | | |
|---|---|---|---|
| 5,288,629 A | 2/1994 | Berkner | |
| 5,580,560 A | 12/1996 | Nicolaisen et al. | |
| 5,874,407 A | 2/1999 | Kelley et al. | |
| 5,994,296 A | 11/1999 | Ruf et al. | |
| 7,026,524 B2 * | 4/2006 | Persson et al. ............... | 800/8 |
| 2003/0096338 A1 | 5/2003 | Pedersen et al. | |
| 2003/0130191 A1 | 7/2003 | Persson et al. | |

| | | |
|---|---|---|
| 2003/0170863 A1 | 9/2003 | Perrsson et al. |

FOREIGN PATENT DOCUMENTS

| | | |
|---|---|---|
| EP | 0 200 421 B1 | 7/1993 |
| JP | 10-58966 A | 8/1998 |
| JP | 2001-061479 | 3/2001 |
| WO | WO 88/10295 | 12/1988 |
| WO | WO 94/07515 | 4/1994 |
| WO | WO 94/27631 | 12/1994 |
| WO | WO 96/12800 | 5/1996 |
| WO | WO 97/20939 | 6/1997 |
| WO | WO 98/31394 | 7/1999 |
| WO | WO 01/158935 A2 | 8/2001 |
| WO | WO 01/75086 A2 | 10/2001 |
| WO | WO 01/82943 A2 | 11/2001 |
| WO | WO 01/83725 A1 | 11/2001 |
| WO | WO 01/85198 A1 | 11/2001 |
| WO | WO 02/22776 A2 | 3/2002 |
| WO | WO 02/38162 A1 | 5/2002 |
| WO | WO 02/062376 A1 | 8/2002 |
| WO | WO 02/077218 A1 | 10/2002 |
| WO | WO 03/027147 A2 | 4/2003 |

OTHER PUBLICATIONS

U.S. Appl. No. 10/295,682, filed Nov. 15, 2002, Persson et al.
U.S. Appl. No. 60/184,036, filed Feb. 22, 2000, Pedersen et al.
Iakhiaev, et al., "The Role of Catalytic Cleft and Exosite Residues of Factor VIIa for Complex Formation with Tissue Factor Pathway Inhibitor", *Thromb Haemost* vol. 85, pp. 458-463 (2001).
Chang et al., "Engineered Recombinant Factor VII $Q^{217}$ Variants with Altered Inhibitor Specificities", *Biochemistry*, vol. 38, pp. 10940-10948 (1999).
Mizuguchi et al., Abstract 1474, Journ of Int. Soc. Of Thromb and Haemo. Suppl.; p. 466 (Aug. 1999).
Leonard et al., Abstract 1473, Journ of Int. Soc. Of Thromb and Haemo. Suppl.; p. 466 (Aug. 1999).

(Continued)

*Primary Examiner*—Kathleen M. Kerr
*Assistant Examiner*—Holly Schnizer
(74) *Attorney, Agent, or Firm*—Thomas Fitting

(57) ABSTRACT

A modified factor VIIa is provided. The modified factor has increased amidolytic activity in the absence of T.F. and a higher affinity for T.F. when compared to the native factor VIIa but does not have substantially altered proteolytic activity when bound to T.F. Nucleic acid molecules that encode the factor, expression vectors that contain the nucleic acid molecules, cells that contain the nucleic acid molecules, and cells transformed with the expression vector are also provided. In a preferred embodiment, the modified factor is a human factor VIIa.

15 Claims, 1 Drawing Sheet

OTHER PUBLICATIONS

Jin, "Structure-Function Study of Blood Coagulation Factor VII by In Vitro Mutagenesis and Computer Simulation", *UMI Dissertation Services*, pp. ii-114 (1999).

Jin et al., "Four Loops of the Catalytic Domain of Factor VIIa Mediate the Effect of the First EGF-like Domain Substitution on FActor VIIa Catalytic Activity", *Journ of Molec Bio.*, vol. 307, Part. 5, pp. 1503-1517, Abstract only.

Persson et al., "Substitution of Valine for Leucine 305 in Factor VIIa Increases the Intrinsic Enzymatic Activity", *Journ of Biol Chem* vol. 276 (31), pp. 29195-29199 (2001).

Peyvandi et al., "Molecular Characterization and Three-Dimensional Structural Analysis of Mutations in 21 Unrelated Families with Inherited Factor VII Deficiency", *Throm Haemost*, vol. 84, pp. 250-257 (2000).

Peyvandi et al., "Two Naturally Occurring Mutations on FVII Gene (S3631-W364C) Altering Intrinsic Catalytic Activity", *Throm Haemost*, vol. 88, pp. 750-755 (2002).

Stenesh J., Diet of Biochem and Molec Bio 2nd ED. p. 97 (Oct. 18, 1989).

Kumar, et al., "Specific Molecular Interaction Sites on Factor VII Involved in Factor X Activation", *Europ Journ of Biochem* vol. 217 (2) pp. 509-518 (1993).

Soejima, et al., "Factor VIIa Modified in the 170 Loop Shows Enhanced Catalytic Activity but Does Not Change the Zymogen-like Property", *Journ of Bio Chem.*, vol. 276 (20), pp. 17229-17235 (2001).

Bernardi, et al., "Mutation Pattern in Clinically Asymptomatic Coagulation Factor VII Deficienty", *Human Mutation* vol. 8 pp. 108-115 (1996).

Dickinson, et al., "Identification of Surface Residues Mediating Tissue Factor Binding and Catalytic Function of the Serine Protease Factor VIIa" *Proc Natl Acad Sci USA*, vol. 93, pp. 14379-14384 (96).

Neuenschwander, et al., Alteration of the Substrate and Inhibitor Specificities of Blood Coagulation Factor VIIa: Importance of Amino Acid Residue $K^{191}$ *Biochemistry* vol. 34 pp. 8701-8707 (1995).

Persson, et al., "Rational Design of Coagulation Factor VIIa Variants with Substantially Increased Intrinsic Activity", *Proc. Natl. Acad. Sci.* vol. 98, pp. 135583-135588 (2001).

Petrovan, et al., "Residue $Met^{156}$ Contributes to the Labile Enzyme Conformation of Coagulation Factor VIIa", *The Journal of Biological Chemistry* vol. 276, pp. 6616-6620 (2001).

\* cited by examiner

MODIFIED FACTOR VIIA

CROSS REFERENCE TO RELATED APPLICATION

This application is a continuation-in-part of U.S. Provisional Patent Application Ser. No. 60/247,589, filed Nov. 9, 2000.

Funds used to support some of the studies reported herein were provided by the National Institutes of Health (NIH Grant HL48752). The United States Government, therefore, has certain rights in this invention.

TECHNICAL FIELD OF THE INVENTION

The field of this invention is coagulation. More particularly, the present invention pertains to a novel form of coagulation factor VIIa and uses of that novel factor.

BACKGROUND OF THE INVENTION

Allosteric regulation of catalytic activity of the serine protease factor VIIa (VIIa) is utilized as a mechanism to control the initiation of the coagulation pathways (Ruf, W. and Dickinson, C. D. (1998) *Trends Cardiovasc. Med.* 8, 350–356). VIIa circulates in the blood plasma as zymogen as well as the cleaved two chain enzyme (Seligsohn, U., Kasper, C. K., Osterud, B., and Rapaport, S. I. (1979) *Blood* 53, 828–837), but proteolytic function only ensues upon binding to its cell surface receptor and catalytic cofactor tissue factor (TF). TF has two distinct effects that regulate proteolysis by VIIa. First, TF provides affinity for macromolecular substrate by contributing to an extended exosite together with the bound VIIa γ-carboxyglutamic acid-rich (Gla) domain. This exosite is a binding site for the factor X Gla-domain (Ruf, W., Miles, D. J., Rehemtulla, A., and Edgington, T. S. (1992) *J. Biol. Chem.* 267, 6375–6381; Huang, Q. L., Neuenschwander, P. F., Rezaie, A. R., and Morrissey, J. H. (1996) *J. Biol. Chem.* 271, 21752–21757; and Ruf, W., Shobe, J., Rao, S. M., Dickinson, C. D., Olson, A., and Edgington, T. S. (1999) *Biochemistry* 38, 1957–1966). Second, TF enhances catalytic activity by allosteric effects on the VIIa protease domain. In the absence of cofactor, VIIa has only very low catalytic activity towards small peptidyl substrate mimetics and TF stimulates the amidolytic of VIIa up to 100-fold. However, macromolecular substrate factor X scissile bond catalysis is enhanced >1000-fold (Ruf, W., Rehemtulla, A., Morrissey, J. H., and Edgington, T. S. (1991) *J. Biol. Chem.* 266, 2158–2166), indicating that cofactor-induced conformational changes may influence extended macromolecular substrate recognition regions in addition to the S1–S3 subsite that is probed by the small substrates.

The low catalytic activity of free VIIa results from a zymogen-like conformation of the enzyme. Upon zymogen cleavage, serine protease domains typically undergo a conformational ordering of loop segments, termed the activation domain (Huber, R. and Bode, W. (1978) *Accounts Chem. Res.* 11, 114–122), resulting in the formation of an activating canonical salt bridge of $Asp^{343}$ with the newly generated amino-terminal $Ile^{153}$. In the absence of cofactor, VIIa shows an increased susceptibility of the amino-terminus to chemical modification (Higashi, S., Nishimura, H., Aita, K., and Iwanaga, S. (1994) *J. Biol. Chem.* 269, 18891–18898), indicating exposure of $Ile^{153}$ that can result from an alternative conformation or increased flexibility and disorder in the activation pocket of free VIIa. The structural determinants for the propensity of VIIa to stay in a zymogen-like conformation have not been investigated. Available structures of free and TF-bound VIIa (Banner, D. W., D'Arcy, A., Chène, C., Winkler, F. K., Guha, A., Konigsberg, W. H., Nemerson, Y., and Kirchhofer, D. (1996) *Nature* 380, 41–46; Zhang, E., St. Charles, R., and Tulinsky, A. (1999) *J. Mol. Biol.* 285, 2089–2104; Pike, A. C. W., Brzozowski, A. M., Roberts, S. M., Olsen, O. H., and Persson, E. (1999) *Proc. Natl. Acad. Sci. USA* 96, 8925–8930; Kemball-Cook, G., Johnson, D. J. D., Tuddenham, E. G. D., and Harlos, K. (1999) *J. Struct. Biol.* 127, 213–223; and Dennis, M. S., Eigenbrot, C., Skelton, N. J., Ultsch, M. H., Santell, L., Dwyer, M. A., O'Connell, M. P., and Lazarus, R. A. (2000) *Nature* 404, 465–470) did not provide mechanistic insight, since in each case the active site of VIIa was occupied with inhibitors that are known to stabilize the $Ile^{153}$-$Asp^{343}$ saltbridge (Higashi, S., Matsumoto, N., and Iwanaga, S. (1996) *J. Biol. Chem.* 271, 26569–26574) and restrict conformational flexibility in the VIIa protease domain (Dickinson, C. D., Shobe, J., and Ruf, W. (1998) *J. Mol. Biol.* 277, 959–971). Mutational studies also failed to elucidate the basis for the labile enzyme conformation, because the taken approaches mainly probed the active enzyme in the TF-VIIa complex (Dickinson, C. D., Kelly, C. R., and Ruf, W. (1996) *Proc. Natl. Acad. Sci. USA* 93, 14379–14384).

This study investigates the role of residue $Met^{298}$ in maintaining the zymogen-like conformation of VIIa. This residue is located within the activation pocket, covering $Ile^{153}$ upon amino-terminal insertion (Banner, D. W., D'Arcy, A., Chène, C., Winkler, F. K., Guha, A., Konigsberg, W. H., Nemerson, Y., and Kirchhofer, D. (1996) *Nature* 380, 41–46). The conformation of the 298 side chain can influence the catalytic activity of serine protease domains. In the case of tissue plasminogen activator (tPA) (Renatus, M., Engh, R. A., Stubbs, M. T., Huber, R., Fischer, S., Kohnert, U., and Bode, W. (1997) *EMBO J.* 16, 4797–4805; and Tackiest, K. and Madison, E. L. (1997) *J. Biol. Chem.* 272, 28–31) and vampire bat plasminogen activator (Renatus, M., Stubbs, M. T., Huber, R., Bringmann, P., Donner, P., Schleuning, W.-D., and Bode, W. (1997) *Biochemistry* 36, 13483–13493), $Lys^{298}$ can substitute for $Ile^{153}$ to form an activating salt bridge with $Asp^{343}$, resulting in efficient catalysis in the absence of zymogen cleavage. However, Lys at this position is found in a large number of serine proteases without conferring catalytic activity in the zymogen precursors, indicating that multiple interactions within the activation pocket determine the activation state of serine protease domains. Whereas Lys or other hydrophilic side chains are predominant in serine proteases that undergo spontaneous ordering of the activation pocket upon zymogen cleavage, VIIa has a Met residue in the 298 position. We hypothesized that the side chain property of $Met^{298}$ is one of the determinants that interfere with the acquisition of full catalytic activity of VIIa upon zymogen cleavage. This study demonstrates that replacement of $Met^{298}$ with Gln, the side chain found in factor IX, had little effect on the activity of TF-bound VIIa. However, free $VIIa_{Gln298}$ had enhanced catalytic function towards macromolecular and small peptidyl substrates. These experiments thus identify the first residue side chain that is one of the determinants for the zymogen-like conformation of the VIIa protease domain.

BRIEF SUMMARY OF THE INVENTION

In one embodiment, the present invention provides a modified factor VIIa. Pharmaceutical compositions comprising the modified factor, nucleic acid molecules that encode the factor, expression vectors that contain the nucleic acid molecules, cells that contain the nucleic acid molecules, and cells transformed with the expression vector are also provided. In a preferred embodiment, the modified factor is a human factor VIIa.

The modified factor VIIa compounds of the present invention have increased amidolytic activity in the absence of TF when compared to the native factor VIIa, and a higher affinity for TF, but do not have a substantially altered proteolytic activity when bound to T.F. The modified factor VIIa compounds of the present invention are characterized as having at least one of three amino acid residue modifications when compared to native factor VIIa. The three modifications are: a glutamine residue at position 298, an isoleucine residue at position 296 and an asparagine residue at position 158. In a preferred embodiment, a modified factor VIIa has at least two of those modifications.

In another embodiment, the factor has been further modified to increase its stability. In accordance with this embodiment, at least one lysine, arginine, isoleucine, phenylalanine or tyrosine residue selected from the group consisting of lysine (38), lysine (32), arginine (290), arginine (315), lysine (341), arginine (304), isoleucine (42), tyrosine (44), phenylalanine (278), and tyrosine (332) has been replaced with an amino acid that provides a proteolytically more stable peptide bond.

In yet another embodiment, this invention provides a method for the treatment of a bleeding disorder in a patient. The method includes the step of administering to the patient a pharmaceutical composition comprising the modified factor VIIa.

Serine protease activation is typically controlled by proteolytic cleavage of the scissile bond, resulting in spontaneous formation of the activating $Ile^{153}$-$Asp^{343}$ saltbridge. The initiating coagulation protease factor VIIa (VIIa) differs by remaining in a zymogen-like conformation that confers the control of catalytic activity to the obligatory cofactor and receptor tissue factor (T.F.). This study demonstrates that the unusual hydrophobic $Met^{298}$ residue contributes to the propensity of the VIIa protease domain to remain in a zymogen-like conformation. Mutation of $Met^{298}$ to Gln, which is found in the same position of the highly homologous factor IX, had no influence on the amidolytic and proteolytic activity of T.F.-bound VIIa. Furthermore, the mutation did not appreciably stabilize the labile $Ile^{153}$-$Asp^{343}$ salt-bridge in the absence of cofactor. $VIIa_{Gln298}$ had increased affinity for T.F., consistent with a long-range conformational effect that stabilized the cofactor binding site in the VIIa protease domain. Notably, in the absence of cofactor amidolytic and proteolytic function of $VIIa_{Gln298}$ were enhanced 3- and 9-fold, respectively, compared to wild-type VIIa. The mutation thus selectively influenced the catalytic activity of free VIIa, identifying the $Met^{298}$ residue position as a determinant for the zymogen-like properties of free VIIa.

The low catalytic activity of the serine protease factor VIIa (VIIa) in the absence of the cofactor tissue factor (TF) results from a zymogen-like conformation of the enzyme. Binding of TF induces a conformational ordering of the protease domain of VIIa and as a consequence increases catalytic function, providing a mechanism strictly control the initiation of the coagulation cascade through the expression of the cell surface receptor TF. Three different mutational effects shed light on the regions that determine the zymogen-like features of VIIa and the ordering the protease domain upon cofactor binding. First, Pro replacement of $Phe^{374}$, a buried aromatic residue side chain common to allosterically regulated serine proteases, severely impaired TF-mediated enhancement of catalytic function, but had no effect on the activity of free VIIa nor on the cofactor-induced stabilization of the amino-terminal insertion, as measured as the susceptibility of $Ile^{153}$ to chemical modification. This demonstrates that the stability of the $Ile^{153}$-$Asp^{343}$ saltbridge is not a direct correlate of changes in catalytic activity, but rather reflects only one of the cofactor-induced effects in the VIIa protease domain. This notion is further supported by a second type of mutations, either within the interface with TF or within the 180's loop, that completely lacked stabilization of the $Ile^{153}$-$Asp^{343}$ saltbridge, but nevertheless showed significantly enhanced function by TF binding. A similar divergence of changes in catalytic activity and stability of the amino-terminal insertion, is documented for a third type of mutant, exemplified by the replacement of $Met^{298}$ by Gln, the side chain found in the homologous factor IXa. This mutation had no significant influence on the catalytic activity of the TF-bound VIIa. In the absence of TF, however, $VIIa_{Gln298}$ displayed increased amidolytic and proteolytic activity, without displaying a significant protection of the amino-terminus from chemical modification. Introduction of the $Gln^{298}$ side chain may stabilize $Gln^{296}$ to partially reverse the zymogen-like conformation of free VIIa through conformational changes in the 285–296 loop. This loop requires ordering during zymogen to enzyme transition and was found reoriented upon allosteric inhibitor binding to VIIa. The analysis of these mutants thus provides novel insight into structural determinants that retain VIIa in a zymogen-like state and into the specific conformational framework that leads to catalytic activation of VIIa by cofactor binding. This study also demonstrates that it is feasible to increase affinity for TF as well catalytic function in engineered VIIa molecules that may offer advantages as improved VIIa-based anti-hemophilic agents.

BRIEF DESCRIPTION OF THE DRAWINGS

In the drawings that form a portion of the specification

DETAILED DESCRIPTION OF THE INVENTION

Figure 1:
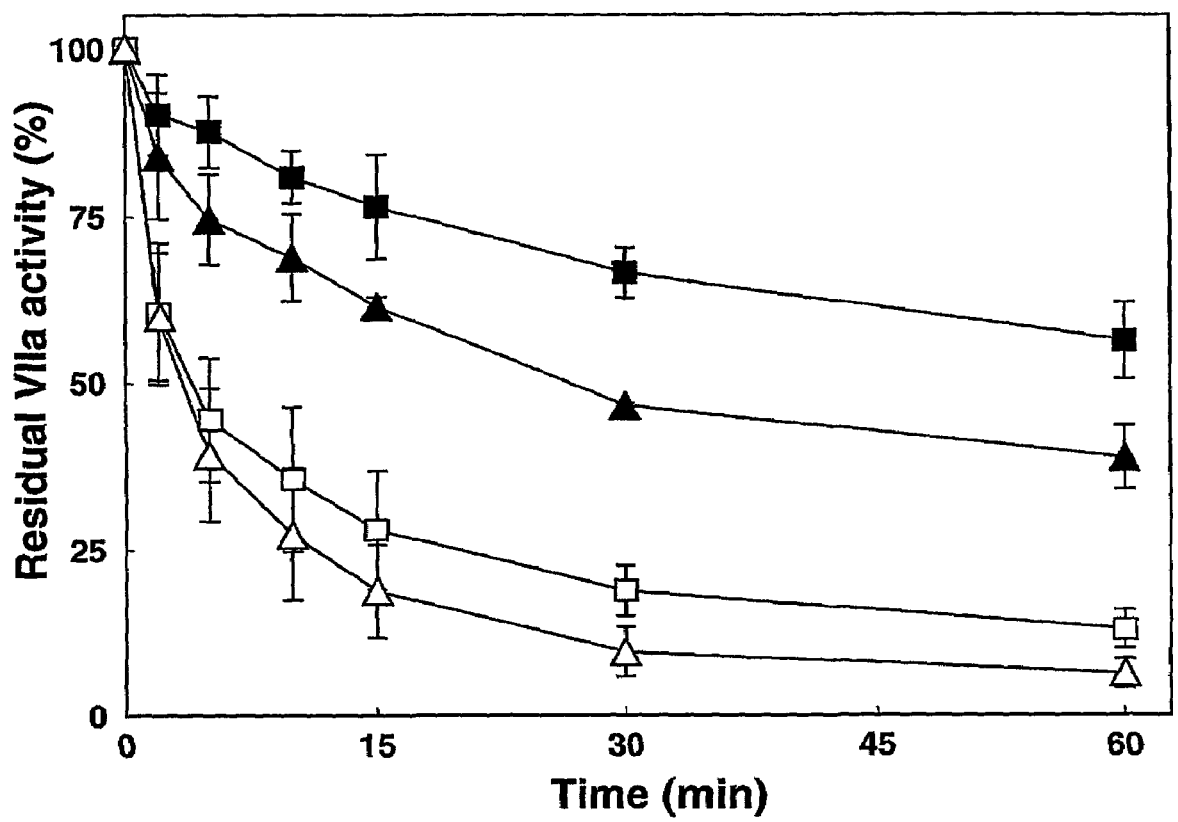
FIG. 1 shows inhibition of wild-type VIIa (squares) or $VIIa_{Gln298}$ (triangles) by antithrombin III/heparin. Residual amidolytic activity was determined after the indicated times of incubation of 100 nM free VIIa (filled symbols) or 50 nM VIIa in complex with 250 nM $TF_{1-218}$ (open symbols) with 0.5 µM antithrombin III in the presence of 5 U/ml unfractionated heparin at 37° C. in TBS, 5 mM $CaCl_2$, and 0.2% bovine serum albumin.

For factor VIIa, biological activity is characterized by the mediation of blood coagulation through the extrinsic pathway. Factor VIIa activates factor X to factor Xa, which in turn converts prothrombin to thrombin thereby initiating the formation of a fibrin clot.

"Factor VIIa" as used in this application includes proteins that have the amino acid sequence of native human factor VIIa. It also includes proteins with a slightly modified amino acid sequence, for instance, a modified C-terminal end including C-terminal amino acid deletions or additions so long as those proteins substantially retain the activity of factor VIIa. Also, degree and location of glycosylation or other post-translation modifications may vary depending on the chosen host cells and the nature of the host cellular environment.

"Modified factor VIIa" shall mean a biologically active molecule derived from factor VIIa by the substitution or deletion of one or more amino acid residues.

The number system of the amino acid sequence of factor VIIa used herein corresponds to the numbering system of mature VIIa in which the N-terminal alanine is numbered 1 and the C-terminal proline is numbered 406.

The three letter and one letter abbreviations used for the amino acids are those as normally used in the art, i.e.:

| Alanine | Ala | A |
|---|---|---|
| Cysteine | Cys | C |
| Aspartate | Asp | D |
| Glutamate | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |
| .gamma.-carboxyglutamic acid | Gla | V |

The zymogen-like conformation of VIIa is required to subject the regulation of VIIa's catalytic activity under strict control of the cell surface expression of the cofactor T.F. The labile enzyme conformation of VIIa allows for the presence of significant amounts of the two chain enzyme in the circulating blood and thus for the initiation of the coagulation pathways, as soon as the cofactor is exposed upon disruption of vascular integrity. This mechanism of triggering an enzyme cascade differs from the activation of the fibrinolytic system by tPA, which utilizes a catalytically active zymogen for the initial proteolytic events. Whereas an activating salt-bridge of $Lys^{298}$ with $Ile^{153}$ has been defined as the structural basis for the active zymogen conformation of tPA (Renatus, M., Engh, R. A., Stubbs, M. T., Huber, R., Fischer, S., Kohnert, U., and Bode, W. (1997) *EMBO J.* 16,4797–4805; and Tackiest, K. and Madison, E. L. (1997) *J. Biol. Chem.* 272, 28–31), structural determinants of the labile enzyme conformation of VIIa remained unclear from previous structural and mutational studies. Here, we provide evidence that the hydrophobic $Met^{298}$ residue side chain within the activation pocket, in part, is responsible for the zymogen-like conformation of the VIIa protease domain.

Replacement of $Met^{298}$ by Gln, the side chain found in factor IX, did not appreciably influence catalytic function of the T.F.-bound enzyme towards small chromogenic substrates or the macromolecular substrate factor X. Thus, the cofactor-stabilized, active conformation of VIIa does not absolutely require a Met side chain at this position. Backbone-superimposition of the structures of porcine factor IXa (Brandstetter, H., Bauer, M., Huber, R., Lollar, P., and Bode, W. (1995) *Proc. Natl. Acad. Sci. USA* 92, 9796–9800) and VIIa in the T.F.-VIIa complex (Banner, D. W., D'Arcy, A., Chène, C., Winkler, F. K., Guha, A., Konigsberg, W. H., Nemerson, Y., and Kirchhofer, D. (1996) *Nature* 380, 41–46) demonstrate that essentially the same space is occupied by the Met and Gln side chains in the respective proteases, providing a structural rational why the Gln replacement is permissive for function of the T.F.-bound VIIa. However, free $VIIa_{Gln298}$ displayed increased function compared to wild-type VIIa. First, the mutant had higher affinity for T.F. and affinity was not appreciably influenced by active site inhibitor binding that typically slows dissociation for wild-type VIIa and for most of the previously characterized mutants (Dickinson, C. D., Shobe, J., and Ruf, W. (1998) *J. Mol. Biol.* 277, 959–971). The cofactor binding site of $VIIa_{Gln298}$ thus appears to be altered, indicating a long range conformational change of the residue replacement of $Met^{298}$ by Gln in the activation pocket. Second, $VIIa_{Gln298}$ had higher amidolytic and proteolytic activity in the absence of cofactor. Amidolytic activity was enhanced 3-fold, whereas activation of factor X was increased 9-fold in the presence or absence of phospholipid. The difference in enhancement may result from an additional ordering of regions that influence macromolecular substrate scissile bond cleavage, but not the hydrolysis of p-nitroanilide chromogenic substrates which bind primarily to the S1–S3 subsites of the catalytic cleft.

Because stabilization of the amino-terminal $Ile^{153}$-$Asp^{343}$ salt-bridge is generally considered to be the major determinant for the activation state of the VIIa protease domain, it was surprising that chemical modification of the amino-terminal $Ile^{153}$ in free $VIIa_{Gln298}$ was little different from wild-type VIIa. However, we have found poor correlation of cofactor-mediated catalytic enhancement and susceptibility of the amino-terminus to chemical modification in a number of other VIIa mutants. Most importantly, certain mutations in the T.F.-binding interface of the VIIa protease domain resulted in a complete failure to show protection of the amino-terminus upon cofactor binding, but T.F. was still able to enhance amidolytic activity of these VIIa mutants by >10-fold. Stabilization of the insertion of the amino-terminus, as measured by the susceptibility to chemical modification, is thus not absolutely required for changes in catalytic function of VIIa to occur.

The local environment at the 298 position in VIIa differs from other homologous coagulation factors, such as factor IXa. Whereas porcine factor IXa has a hydrophobic Ile residue in the 296 position along with a pair of charged residues at position 158(Asn) and 298 (Gln), VIIa has a charged $Glu^{296}$ and a pair of hydrophobic residues, i.e. $Val^{158}$ and $Met^{298}$. One or two water molecules (not shown) are consistently resolved between the $Glu^{296}$ and $Met^{298}$ side chain in structures of the T.F.-VIIa complex (Banner, D. W., D'Arcy, A., Chène, C., Winkler, F. K., Guha, A., Konigsberg, W. H., Nemerson, Y., and Kirchhofer, D. (1996) *Nature* 380, 41–46; and Zhang, E., St. Charles, R., and Tulinsky, A. (1999) *J. Mol. Biol.* 285, 2089–2104). $Met^{298}$ replacement by Gun in one possible rotamer position that orients the amide of the Gun side chain towards $Glu^{296}$. The low catalytic function of acidic side chain replacement mutants and the high functional activity of amide counterparts (Table 2) indirectly supports the notion that such an orientation of the introduced $Gln^{298}$ is most compatible with optimal activity. The charge complementarity of the $Gln^{298}$ and $Glu^{296}$ side chains may stabilize the-local conformation of this region in free $VIIa_{Gln298}$, possibly involving the coordination of a water molecule between the two side chains. The activating effect of the $Gln^{298}$ mutation may thus be mediated through an effect on the $Glu^{296}$ position, rather then the adjacent amino-terminal insertion.

In wild-type VIIa, Ala mutation of $Glu^{296}$ reduces amidolytic function 3-fold and proteolytic function 6- to 10-fold, displaying some divergence of the mutational effect on amidolytic versus proteolytic function. The free $Gln^{298}$ mutant showed functional enhancement of similar magnitude in both assays, arguing in favor of a function linkage between $Glu^{296}$ and $Gln^{298}$ in $VIIa_{Gln198}$. $Glu^{296}$ together with the adjacent Leu$^{153}$ side chain are within a "hot spot" that is known to allosterically regulate VIIa's catalytic activity. First, Glu$^{296}$ is located within the epitope of an inhibitory monoclonal antibody and crucial for the inhibitory allosteric switch induced by this exosite inhibitor (Shobe, J., Dickinson, C. D., and Ruf, W. (1999) *Biochemistry* 38, 2745–2751). Second, a small peptide inhibitor of VIIa binds to an epitope that includes Leu$^{153}$ (Dennis, M. S., Eigenbrot, C., Skelton, N. J., Ultsch, M. H., Santell, L., Dwyer, M. A., O'Connell, M, P., and Lazarus, R. A. (2000) *Nature* 404, 465–470). This exosite inhibitor influences catalytic function by a major reorientation of the 142–296 "autolysis" loop that also contains specific residues involved in extended macromolecular substrate recognition (Ruf, W. (1994) *Biochemistry* 33, 11631–11636). The 285–296 loop is considered part of the activation domain, and stabilization and ordering of this loop is essential for the zymogen to enzyme transition. Structural studies on prothrombin derivatives (Vijayalakshmi, J., Padmanabhan, K. P., Mann, K. G., and Tulinsky, A. (1994) *Protein Science* 3, 2254–2271) further suggest that the 285–296 loop can behave as a partially autonomous region of the activation domain. The enhanced function of VIIa$_{Gln298}$ in the absence of a stabilization of the amino-terminal insertion is thus consistent with a conformational effect on the 285–296 loop through the proximity of Glu$^{296}$ with Gln$^{298}$.

The present disclosure also teaches that additional mutations in the sequence of VIIa can further improve the function of VIIa. By way of example, inclusion of an asparagine residue at position 158 or an isoleucine at position 296 enhance the effects of the Gln$^{298}$ mutation (See, Table 1, below).

TABLE 1

| | Amidolytic Activity −T.F. +T.F. (arbitrary units) | Enhancement by T.F. (fold) | Affinity for T.F. Kdapp (pM) | Proteolytic Activity Xa Generation (nMXa/min) |
|---|---|---|---|---|
| wild-type | 0.9 | 25 | 28 | 14 | 9 |
| 298Q | 4.3 | 19 | 4 | 5 | 12 |
| 298Q/158N | 2.6 | 13 | 5 | 4 | 10 |
| 298Q/296I | 5.0 | 13 | 2.5 | 4 | 7 |
| 298Q/158N/296I | 9.2 | 11 | 1.2 | 4 | 10 |

This study identifies the first residue side chains that contribute to the zymogen-like state of free VIIa. Although a single side chain replacement is insufficient to confer complete spontaneous ordering and full catalytic activity of the VIIa protease domain, the proposed stabilization of the 285–296 loop would achieve one of the necessary conformation orderings in the activation domain. The significantly improved function of free modified VIIa argues that a limited number of side chains are be responsible for retaining VIIa in the zymogen-like conformation. Whether changing the local environment of the activation pocket is sufficient to achieve a fully active VIIa or whether changes in the unique loop segments that contact T.F. are also required remain important questions for further studies.

One of skill in the art will readily appreciate that the mutation disclosed herein can be combined with other mutations to produce a modified factor VIIa having a diverse range of function. Means for producing such modifications can be found in U.S. Pat. Nos. 5,997,864; 6,132,730; 6,039,944 and 5,580,560 (the disclosures of all of which are incorporated herein by reference). By way of example, a modified factor VIIa of the present invention can be stabilized against proteolytic cleavage using the means disclosed in U.S. Pat. No. 5,580,560. Briefly, the U.S. Pat. No. 5,580,560 provides a modified factor VII/VIIa being stabilized against proteolytic cleavage at certain positions in the molecule. More specifically, that patent teaches a modified factor VIIa in which one or more proteolytically sensible peptide bond(s) in native factor VIIa has/have been replaced by a proteolytically more stable peptide bond. This is achieved by modifications at certain positions in the native human factor/VIIa molecule. Such modifications may include removal of certain amino acid residues or replacement of one or more amino acid residues with a different amino acid residue. For instance, a trypsin-like proteolytic cleavage my be hindered by stabilizing the peptide bond on the C-terminal end of certain Arg and/or Lys residues and/or replacement of certain Arg and/or Lys residues with other amino acid residues and/or by removal of certain Arg and/or Lys residues.

In a specific embodiment, modifications are made at one or more of the following trypsin-like cleavage sites: (i) lysine(38)-leucine(39), (ii) lysine(32)-aspartate(33), (iii) arginine (290)-glycine(291), (iv) arginine(315)-lysine(316), (v) lysine(341)-glycine(342), (vi) arginine(304)-leucine (305). In another embodiment, a chymotrypsin-like cleavage site(s) is modified. Furthermore, in yet another embodiment, the chymotrypsin-like site that is modified is a cathepsin G site. In a specific embodiment, the chymotrypsin-like site(s) is selected from the group consisting of: (vii) isoleucine(42)-serine(43), (viii) tyrosine(44)-serine(45), (ix) phenylalanine (278)-serine(279), (x) tyrosine(332)-serine(333). In a preferred embodiment, the cleavage sites modified are (i), (ii), (iii) and (iv) have been found to be the ones most susceptible to proteolytic degradation, while the remaining are of less, quantitative importance.

The modified factor VIIa of the present invention can be produced by various methods known in the art. Production can occur at the gene or protein level. Specifically, factor VIIa can be altered at the gene level by site-specific mutagenesis using procedures known in the art. One approach involves the use of synthetic oligonucleotides to construct a modified factor VIIa with base substitutions. In another embodiment, two complementary oligonucleotides are synthesized, each containing the altered sequence. The duplex that forms after annealing these complementary oligonucleotides, can be joined to a larger DNA molecule by DNA ligase provided that the ends of both molecules have complementary single-stranded "sticky" ends.

Another approach which can be taken involves introducing a small single-stranded gap in the DNA molecule followed by mis-repair DNA synthesis i.e., the misincorporation of a non-complementary nucleotide in the gap (Botstein and Shortle, 1985, Science 229:1193). The incorporation of a thiol nucleotide into the gap may minimize the excision of the non-complementary nucleotide. Alternatively, a factor VII variant may be prepared by chemically synthesizing the DNA encoding the factor VII variant using procedures known in the art (See, for example, Froehler, 1986, *Nucl. Acids Res.* 14:5399–5407 and Caruthers et al., 1982, *Genetic Engineering*. J. K. Setlow and A. Hollaender eds., Plenum Press, N.Y., vol. 4, pp. 1–17). In a preferred embodiment, fragments of the variant factor VIIa are chemically synthesized and these fragments are subsequently ligated together. The resulting modified factor VIIa strands may be amplified using procedures known in the art, e.g. PCR technology and subsequently inserted into a cloning vector. In a specific embodiment, site specific mutants may be created by introducing mismatches into the oligonucleotides used to prime the PCR amplification (Jones and Howard, 1990, *Biotechniques* 8:178–180).

Manipulations of the factor VIIa sequence can be carried out at the protein level. Any of numerous chemical modifications may be carried out by known techniques including but not limited to specific chemical cleavage by cyanogen bromide, trypsin, chymotrypsin, papain, V8 protease, NaBH.sub.4; acetylation, formylation, oxidation, reduction; etc. Alternatively, the variant factor VIIa protein can be chemically synthesized using procedures known in the art, such as commercially available peptide synthesizers and the like. Such standard techniques of polypeptide synthesis can be found described in such publications as Merrifield, 1963, J. Chem. Soc. 85:2149–2296 and Hunkapillar et al., 1984, *Nature* (London) 310:105–111).

The identified and isolated gene or cDNA can then be inserted into an appropriate cloning vector. A large number of vector-host systems known in the art may be used. The vector system must be compatible with the host cell used. Recombinant molecules can be, introduced into host cells via transformation, transfection, infection, electroporation, etc. In specific embodiments, transformation of host cells with recombinant DNA molecules that incorporate an isolated factor VIIa gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA. Once the factor VII-containing clone has been identified, grown, and harvested, its DNA insert can be characterized using procedures known in the art such as Southern hybridization, restriction endonuclease mapping, and DNA sequence analysis.

The modified factor VIIa gene can be isolated and recloned into a suitable expression vector. The expression vector is then transfected into an appropriate host cell which when cultured in a suitable culture medium expresses and secretes the modified factor VIIa, which after recovery from the culture medium, is converted into the corresponding modified factor VIIa by known means. Various host cells may be used including mammalian cells, yeast and other fungi, and bacteria. However, mammalian cells are preferred. For expression of modified factor VIIa according to the invention in cultured mammalian cells, expression vectors containing cloned modified factor VII sequences are introduced into the cells by appropriate transfection techniques, such as calcium phosphate-mediated transfection or electroporation transfection.

Modified factor VIIa produced by the transfected cells can be removed from the cell culture media by adsorption to barium citrate. Further purification may be achieved through immunoadsorption. Alternatively, purification of the barium citrate precipitated material may be accomplished by more conventional biochemical methods or by high-performance liquid chromatography (HPLC).

The modified factor VIIa of the present invention can be used for the treatment of a bleeding disorder, e.g. patients who have developed inhibitors to factor VIII, and platelet disorders including but not limited to thrombocytopenia, von Willebrand's disease and others typically present in association with severe tissue damage in a pharmaceutical composition with an acceptable carrier. The pharmaceutical carriers are such physiologically compatible buffers as Hank's or Ringer's solution, physiological saline, a mixture consisting of saline and glucose. The modified factor VIIa produced by the methods of the present invention can be mixed with colloidal-like plasma substitutes and plasma expanders such as linear polysaccharides (e.g. dextran), hydroxyethyl starch, balanced fluid gelatin, and other plasma proteins. Additionally, the modified factor VIIa may be mixed with water soluble, physiologically acceptable, polymeric plasma substitutes, examples of which include polyvinyl alcohol, poly(ethylene oxide), polyvinylpyrrolidone, and ethylene oxide-polypropylene glycol condensates.

The Examples that follow illustrate preferred embodiments of the present invention and are not limiting of the specification and claims in any way.

EXAMPLE 1

General Methods

Proteins—Wild-type and mutant VIIa were expressed in Chinese hamster ovary (CHO) cells grown in suspension culture in serum-free medium supplemented with vitamin $K_3$. Mutant and wild-type recombinant VII was immunoaffinity purified with a calcium-dependent monoclonal antibody, autoactivated to VIIa at 4° C., followed by ion exchange chromatography on MonoQ, as previously described (Ruf, W. (1994) *Biochemistry* 33, 11631–11636). Factor X was purified from plasma with a final monoclonal antibody affinity step to reduce contamination by plasma VII (Dickinson, C. D., Kelly, C. R., and Ruf, W. (1996) *Proc. Natl. Acad. Sci. USA* 93, 14379–14384). Full-length recombinant human TF, produced from insect cells, was reconstituted into 30% phosphatidylserine/70% phosphatidylcholine (PCPS), as described (Ruf, W. and Edgington, T. S. (1991) *Proc. Natl. Acad. Sci. USA* 88, 8430–8434). The soluble extracellular domain of TF ($TF_{1-218}$) was expressed in *E. coli* and refolded from inclusion bodies (Stone, M. J., Ruf, W., Miles, D. J., Edgington, T. S., and Wright, P. E. (1995) *Biochem. J.* 310, 605–614). The Kunitz-type inhibitor 5L15 selected for VIIa specificity by phage-display (Jespers, L. S., Messens, J. H., De Keyser, A., Eeckhout, D., Van Den Brande, I., Gansemans, Y. G., Lauwereys, M. J., Vlasuk, G. P., and Stanssens, P. E. (1995) *Biotechnology* 13, 378–382) was kindly provided by Dr. George Vlasuk (Corvas International, San Diego, Calif.).

Functional assays—Kinetic parameters for factor X activation were determined at fixed concentration (200 pM) of TF reconstituted in PCPS (TF/PCPS) and excess wild-type or mutant VIIa (1 nM) in Hepes buffer saline (BBS, 10 mM Hepes, 150 mM NaCl, pH 7.4), 5 mM $CaCl_2$, 0.2% bovine serum albumin. After a brief incubation at 37° C. to allow TF-VIIa complex formation, factor X (8 nM to 1 µM) was added, and factor Xa was quantified with the chromogenic substrate Spectrozyme FXa (American Diagnostica, Greenwich, Conn.) in samples quenched with 100 mM EDTA. Initial rates of factor Xa generation, based on calibration curves made with purified Xa, were fitted to the Michaelis-Menten equation using least squares regression analysis. For the determination of the proteolytic activity of free VIIa, 250 nM VIIa was incubated with 1 µM factor X at 37° C. in the presence or absence of 100 µM PCPS, followed by determination of factor Xa generation by chromogenic assay. Kinetic parameters for chromogenic substrate hydrolysis (Chromozym tPA, Roche) were determined at fixed enzyme concentration (60 nM in the absence of T.F. or 30 nM in the presence of 120 nM $TF_{1-218}$) with varying concentrations of substrate (0.02–2 mM) in Tris-buffered saline (TBS, 20 mM Tris, 150 mM NaCl, pH 8.0), 5 mM $CaCl_2$, and 0.2% bovine serum albumin at ambient temperature. Initial rate data were fitted to the Michaelis-Menten equation using least squares regression analysis.

VII mutants were expressed in transient transfection experiments and expression levels were determined by immunoassay. Proteolytic activities of mutants were analyzed in a functional assay at 37° C. in HBS, 5 mM $CaCl_2$, and 0.2% bovine serum albumin. A fixed concentration of T.F./PCPS (5 pM) was saturated with increasing concentrations of mutant or wild-type VIIa, followed by addition of 50 nM factor X and determination of factor Xa generation by amidolytic assay. The maximum rate of Xa generation as a measure of the proteolytic function of the mutant VIIa in complex with T. F. was calculated based on calibration curves made with purified Xa.

EXAMPLE 2

Characteristics of Modified Factor VIIa

Carbamylation of $Ile^{153}$ in VIIa—Chemical modification of the amino-terminal $Ile^{153}$ of wild-type or mutant VIIa was performed at ambient temperature according to Higashi et al. (Higashi, S., Nishimura, H., Aita, K., and Iwanaga, S. (1994) *J. Biol. Chem.* 269, 18891–18898). Free VIIa (4 µM or VIIa (1 µM) in complex with $TF_{1-218}$ (4 pM) was reacted with 0.2 M KCNO in HBS, 5 mM $CaCl_2$ for various times. Samples were withdrawn, diluted 25- or 60-fold for free or TF-bound VIIa, respectively, and the residual amidolytic activity was determined with 0.7 mM Chromozym tPA. Rates of inactivation were calculated from a plot of the residual activity (in % of the initial activity) versus incubation time.

Inhibition of VIIa by antithrombin II/Heparin—To analyze the time dependence of inhibition of free VIIa (100 nM) or VIIa (50 nM) in complex with $TF_{1-218}$ (250 nM) by antithrombin III/heparin, wild-type and mutant VIIa were reacted with 0.5 µM antithrombin III (Haematologic Technologies, VT) in the presence of 5 U/ml unfractionated heparin (Elkins-Sinn, N.J.), at 37° C. in TBS, 5 mM $CaCl_2$, and 0.2% bovine serum albumin. After defined times (2 to 60 min) samples were diluted into the chromogenic substrate Chromozym tPA (1.5 mM and the residual amidolytic activity was immediately determined in a kinetic microplate reader.

Surface plasmon resonance analysis—Binding constants for wild-type and mutant VIIa were analyzed using a BIAcore 2000 instrument (Pharmacia Biosensor). A non-inhibitory anti-T.F. antibody (TF9–10H10) was directly immobilized by amino-coupling to an activated dextran matrix for capture of full-length recombinant T.F., as described previously (Dickinson, C. D. and Ruf, W. (1997) *J. Biol. Chem.* 272, 19875–19879). TF was injected to saturate the antibody and association data were collected from injections of five concentrations (25 nM to 1 µM) of VIIa in HBS, 5 mM $CaCl_2$ 0.005% surfactant P20 and 3 mM CHAPS. Binding kinetics in the presence of the Kunitz-type inhibitor 5L15 were determined by premixing VIIa with 10 µM 5L15. Dissociation data were collected for 250 s after return to buffer flow and the chip surface was regenerated with pulses of 0.1 M EDTA and 4 M $MgCl_2$. Dissociation of TF from the antibody could not be detected over a 6 hour period under the standard buffer conditions, and the measured dissociation upon injection of VIIa thus reflects dissociation of the TF-VIIa complex, rather than the release of T.F. from the immobilized antibody. Association and dissociation constants ($k_{on}$ and $k_{off}$) were determined Mutational analysis of position 298 in VIIa—As a first step to define the role of the 298 residue position in catalytic activity of VIIa, we characterized the proteolytic function of various side chain replacements in transient transfection experiments. Maximum rates of factor Xa generation were determined by saturating a fixed concentration of phospholipid reconstituted T.F with the aim to define permissive mutations that do not interfere with amidolytic and proteolytic function of T.F.-bound VIIa. Changing the 298 position to Lys, as found in the highly homologous factor X, resulted in diminished function. In contrast, a Gln side chain, as found in factor IX of all species and in the majority of chymotrypsin-like serine proteases, allowed for normal or slightly enhanced proteolytic function, as compared to wild-type VIIa (See Table 2, below).

TABLE 2

| | $V_{max}$ (nM Xa/min) |
|---|---|
| wild-type | 7.9 ± 0.5 |
| Met298 to Lys | 1.7 ± 0.4 |
| Met298 to Gln | 10.1 ± 1.2 |
| Met298 to Glu | 1.2 ± 0.3 |
| Met298 to Asn | 4.8 ± 0.8 |
| Met298 to Asp | 0.1 ± 0.02 |
| Met298 to Ala | 2.6 ± 0.5 |
| Met298 to Val | 2.8 ± 0.3 |
| Met298 to Ser | 2.6 ± 0.6 |

Negatively charged residues, such as Glu and Asp, were consistently less well tolerated than their respective amide counterparts. In the case of Asn, ~60% of wild-type activity was retained. Only Gln at 298 produced a fully functional VII molecule, although a number of smaller side chain replacements, such as Ala, Val, or Ser, showed significantly reduced proteolytic function. Thus, replacement of the hydrophobic $Met^{298}$ side chain by the more hydrophilic side chain Gln is the only permissive mutation that allows for normal proteolytic function of the T.F.-VIIa complex.

Effect of the $Met^{298}$ to Gln mutation on T.F. binding—$VII_{Gln298}$ was stably expressed, purified and autoactivated at 4° C. Autoactivation of the mutant appeared to proceed somewhat faster than wild-type VII, but the purified protein showed electrophoretic mobility and >95% conversion to the two chain enzyme indistinguishable from wild-type VIIa. Binding of mutant and wild-type VIIa to antibody captured full-length T.F. was analyzed by surface plasmon resonance measurements. Whereas the mutation had only a minor <2-fold effect on the association rate, $VIIa_{Gln298}$ dissociated from T.F. with a significantly lower rate (See Table 3, below), indicating that the cofactor binding site is in a conformation that allows for tighter binding to T.F.

TABLE 3

| | Binding to $TF_{1-263}$ | | |
|---|---|---|---|
| | $k_{on}$ (×$10^5$ $M^{-1}$ $s^{-1}$) | $k_{off}$ (×$10^{-4}$ $s^{-1}$) | $K_D$ (nM) |
| VIIa | | | |
| wild-type | 2.4 ± 0.6 | 7.4 ± 0.3 | 3.1 |
| Met298 to Gln | 1.3 ± 0.1 | 1.4 ± 0.1 | 1.0 |
| VIIa + 5L15 | | | |
| wild-type | 3.1 ± 0.9 | 2.6 ± 0.1 | 0.8 |
| Met298 to Gln | 2.0 ± 0.3 | 1.2 ± 0.1 | 0.6 |

Active site occupancy of wild-type VIIa by the Kunitz-type inhibitor 5L15 is known to tighten the binding with T.F. by slowing the dissociation rate (Dickinson, C. D. and Ruf, W. (1997) *J. Biol. Chem.* 272, 19875–19879). Whereas 5L15 increased affinity for wild-type VIIa 4-fold, only marginal changes were observed for $VIIa_{Gln298}$. Amidolytic function of mutant or wild-type VIIa were blocked >99% by the inhibitor under the experimental conditions, excluding a loss of inhibitor binding to the mutant as the reason for a lack in the change of binding kinetics. Thus, the conformation of the mutant's protease domain, independent of active site occupancy, appeared to be in a higher affinity state for T.F.

Normal cofactor-mediated stabilization of the amino-terminal insertion—Whereas free VIIa displays a labile enzyme conformation with the α-amino group of $Ile^{153}$ susceptible to chemical modification, cofactor binding induces structural rearrangements resulting in a protected amino-terminus. Because carbamylation of $Ile^{153}$ in VIIa by reaction with KNCO inactivates VIIa (8; Petersen, L. C., Persson, E., and Freskgard, P.-O. (1999) *Eur. J. Biochem.* 261, 124–129), the decrease in the amidolytic activity can be used to determine the rate of modification of the amino-terminus as measure for the stability of the $Ile^{153}$-$Asp^{343}$ salt-bridge. Carbamylation of free enzyme showed a similar rate of inactivation of VIIa$_{Gln298}$ versus wild-type VIIa (6.3±0.4 versus 7.5±0.3% loss of initial activity/10 min), demonstrating that the residue replacement was not sufficient to completely order the activation pocket and to stabilize the $Ile^{153}$-$Asp^{343}$ salt-bridge. In addition, the rate of inactivation of the T.F.-bound mutant was also indistinguishable from wild-type VIIa (1.1±0.1 versus 1.4±0.1% loss of initial activity/10 min). Thus, the Gun replacement for $Met^{298}$ does not appreciable influence the stability of the $Ile^{153}$-$Asp^{343}$ salt-bridge in free or T.F.-bound enzyme.

Enhanced amidolytic activity of VIIa$_{Gln298}$ in the absence of cofactor—The higher affinity binding of VIIa$_{Gln298}$ to T.F. may reflect conformational changes in the cofactor binding site that are associated with increased catalytic function of the mutant in the absence of cofactor. To address this issue, the catalytic activities of wild-type or mutant VIIa were analyzed with small peptidyl substrates. The catalytic efficiency of hydrolysis of Chromozym tPA by free VIIa$_{Gln298}$ was increased 3-fold compared to wild-type VIIa (See Table 4, below), indicating that the Gun side chain stabilizes a more active conformation of the VIIa protease domain.

TABLE 4

| | $K_M$ (mM) | $k_{cat}$ (s$^{-1}$) | $k_{cat}/K_M$ (x 10$^{-3}$ M$^{-1}$ s$^{-1}$) |
|---|---|---|---|
| Free VIIa | | | |
| wild-type | 7.6 ± 1.1 | 12.1 ± 1.5 | 1.6 ± 0.1 |
| Met298 to Gun | 5.3 ± 0.4 | 24.6 ± 1.5 | 4.7 ± 0.1 |
| VIIa + TF$_{1-218}$ | | | |
| wild-type | 1.1 ± 0.04 | 49.1 ± 0.7 | 43.4 ± 1.8 |
| Met298 to Gun | 1.2 ± 0.05 | 49.8 ± 1.7 | 41.4 ± 1.0 |

However, VIIa$_{Gln298}$ in complex with T.F. cleaved the chromogenic substrate indistinguishable from wild-type VIIa. Thus, the side chain replacement selectively influenced the catalytic function of the free enzyme.

Effect of the $Met^{298}$ to Gun mutation on inhibition by antithrombin III—To test whether inhibitor binding to the active site of VIIa$_{Gln298}$ was also enhanced in comparison to wild-type VIIa, inhibition of VIIa activity by a fixed concentration of antithrombin III in the presence of 5 U/ml heparin was studied. Consistent with previous studies (Rao, L. V. M., Rapaport, S. I., and Hoang, A. D. (1993) *Blood* 81, 2600–2607; and Lawson, J. H., Butenas, S., Ribarik, N., and Mann, K. G. (1993) *J. Biol. Chem.* 268, 767–770), amidolytic activity of free VIIa was inefficiently inhibited over time by antithrombin III/heparin (FIG. 2). VIIa$_{Gln298}$ was inhibited at a rate that was approximately twice as fast as the rate of inhibition of wild-type VIIa (50% inhibition in 31±3 min for mutant versus 64±12 min for wild-type VIIa, n=3). inhibition of T.F.-VIIa complexes occurred with significantly faster rates for both mutant and wild-type VIIa, reaching 50% inhibition at 4.5±1.8 min for mutant versus 6.0±1.9 min for wild-type VIIa (n=3). The somewhat more efficient inactivation of VIIa$_{Gln298}$ in the presence of T.F. suggests improved interaction of the serpin with the mutant. This may involve exosite interactions, since mutation of the 298 position in tPA also influenced the interaction with plasminogen activator inhibitor 1 (PAI-1) (Tackiest, K. and Madison, E. L. (1997) *J. Biol. Chem.* 272, 28–31). Thus, the enhanced inhibition of free VIIa$_{Gln298}$ by antithrombin III cannot solely be attributed to a stabilized active conformation of the mutant, but may also involve direct inhibitor binding to the newly introduced Gln side chain.

Increased proteolytic function of free VIIa upon replacement of $Met^{298}$ with Gln—Factor X activation by free VIIa was analyzed in the presence and absence of a negatively charged phospholipid surface (PCPS). In both cases, activation of factor X by VIIa$_{Gln298}$ was enhanced 9-fold compared to wild-type VIIa (See Table 5, below).

TABLE 5

| Factor Xa generation by free VIIa | | |
|---|---|---|
| | $v_{max}$ (nmoles Xa/min/μmole VIIa) | |
| | VIIa | VIIa + PCPS |
| wild-type | 0.15 ± 0.02 | 2.6 ± 0.1 |
| Met298 to Gun | 1.3 ± 0.1 | 23.9 ± 1.1 |

| Factor X activation by VIIa bound to phospholipid reconstituted T.F. | | | |
|---|---|---|---|
| | Kinetic parameters | | |
| | $K_M$ (nM) | $k_{cat}$ (s$^{-1}$) | $k_{cat}/K_M$ (x 10$^8$ M$^{-1}$ s$^{-1}$) |
| wild-type | 61 ± 11 | 8.0 ± 1.4 | 1.3 |
| Met298 to Gun | 68 ± 12 | 10.2 ± 1.9 | 1.5 |

However, only subtle changes in the activation of factor X by VIIa$_{Gln298}$ in complex with phospholipid-reconstituted TF were detected (Table 5), both in regard to $K_M$ and $k_{cat}$. These data demonstrate that macromolecular substrate binding as well as scissile bond cleavage are not affected by the mutation after complex formation with the catalytic cofactor and after acquisition of full catalytic activity. In free VIIa, however, the catalytic function towards the macromolecular substrate is enhanced, consistent with the data for small substrate hydrolysis that also demonstrated selectively increased amidolytic activity of free VIIa$_{Gln298}$.

What is claimed is:

1. A wild-type Factor VII modified by a single substitution at position Met298 relative to wild-type human Factor VII, wherein said substitution is selected from the group consisting of Gln(Q), Glu(E), Asn(N), and Ser(S), wherein the wild-type Factor VII has amidolytic activity.

2. A Factor VII as defined in claim 1, wherein said substitution is M298Q.

3. A pharmaceutical formulation comprising a modified Factor VII as defined in claim 2 and a pharmaceutically acceptable carrier.

4. A method for treating a bleeding disorder, the method comprising administering to a patient in need of such treatment an effective amount of a pharmaceutical formulation as defined in claim 3.

5. An isolated nucleic acid encoding a modified Factor VII as defined in claim 1.

6. A vector comprising an isolated nucleic acid as defined in claim 5.

7. An isolated host cell comprising a nucleic acid as defined in claim 5.

8. A method for producing a modified Factor VII, the method comprising (i) culturing a cell as defined in claim 7 under conditions suitable for expression of the modified Factor VII, and (ii) recovering the modified Factor VII from the culture medium.

9. A wild-type Factor VII as defined in claim 1, wherein said wild-type Factor VII exhibits increased amidolytic activity relative to wild-type human Factor VII.

10. A pharmaceutical formulation comprising a modified Factor VII as defined in claim 1 and a pharmaceutically acceptable carrier.

11. A method for treating a bleeding disorder, the method comprising administering to a patient in need of such treatment an effective amount of a pharmaceutical formulation as defined in claim 10.

12. An isolated nucleic acid encoding a modified Factor VII as defined in claim 1.

13. A vector comprising an isolated nucleic acid as defined in claim 12.

14. An isolated host cell comprising a nucleic acid as defined in claim 12.

15. A method for producing a modified Factor VII, the method comprising (i) culturing a cell as defined in claim 14 under conditions suitable for expression of the modified Factor VII, and (ii) recovering the modified Factor VII from the culture medium.

* * * * *